United States Patent
Shen

(10) Patent No.: US 10,034,781 B2
(45) Date of Patent: Jul. 31, 2018

(54) PROSTHETIC KNEE JOINT WITH BUFFERING AND BRAKING EFFECTS

(71) Applicant: PRO LIMB INTERNATIONAL CORP., New Taipei City (TW)

(72) Inventor: Hsin-Fa Shen, New Taipei (TW)

(73) Assignee: PRO LIMB INTERNATIONAL CORP., New Taipei (TW)

(*) Notice: Subject to any disclaimer, the term of this patent is extended or adjusted under 35 U.S.C. 154(b) by 0 days.

(21) Appl. No.: 15/343,943

(22) Filed: Nov. 4, 2016

(65) Prior Publication Data

US 2017/0165086 A1 Jun. 15, 2017

(30) Foreign Application Priority Data

Dec. 10, 2015 (TW) .............................. 104219873 U

(51) Int. Cl.
  *A61F 2/50* (2006.01)
  *A61F 2/64* (2006.01)
  *A61F 2/68* (2006.01)

(52) U.S. Cl.
  CPC .............. *A61F 2/644* (2013.01); *A61F 2/642* (2013.01); *A61F 2002/503* (2013.01); *A61F 2002/5073* (2013.01); *A61F 2002/6818* (2013.01)

(58) Field of Classification Search
  CPC .. A61F 2/64; A61F 2/642; A61F 2/644; A61F 2/646; A61F 2002/648
  See application file for complete search history.

(56) References Cited

U.S. PATENT DOCUMENTS

| 2014/0188252 A1* | 7/2014 | Sadler ..................... A61F 2/644 623/46 |
| 2015/0230942 A1* | 8/2015 | Karlsson .................. A61F 2/64 623/44 |

OTHER PUBLICATIONS

Kameda. Derwent abstract of JP10165430A 1998. A61F2002/64.*
JPO Translation of JP101665430A.*

* cited by examiner

*Primary Examiner* — Thomas J Sweet
*Assistant Examiner* — Christie Bahena
(74) *Attorney, Agent, or Firm* — Birch, Stewart, Kolasch & Birch, LLP

(57) ABSTRACT

A prosthetic knee joint with buffering and braking effects has an upper connecting base, a linking assembly, a braking assembly, and a lower connecting base. The upper connecting base has two extending arms and an accommodating recess. The linking assembly has two linking arms respectively and pivotally connected to the upper connecting base. The braking assembly has a braking arm protruding into the accommodating recess of the upper connecting base and pivotally connected to the two extending arms. The lower connecting base is connected to the linking assembly and the braking assembly. The upper connecting base, the linking assembly, the braking assembly and the lower connecting base form a four-bar linkage. A cushion between an abutting element and a main body provides a buffering effect during walking. Thus, the prosthetic knee joint has simplified structure and reduced cost and is convenient in assembly and use.

9 Claims, 7 Drawing Sheets

PROSTHETIC KNEE JOINT WITH BUFFERING AND BRAKING EFFECTS

CROSS-REFERENCE TO RELATED APPLICATIONS

This application is based upon and claims priority under 35 U.S.C. 119 from Taiwan Patent Application No. 104219873 filed on Dec. 10, 2015, which is hereby specifically incorporated herein by this reference thereto.

BACKGROUND OF THE INVENTION

1. Field of the Invention

The present invention relates to a prosthetic knee joint with buffering and braking effects.

2. Description of the Prior Arts

A prosthetic knee joint is for assisting the injured or disabled person in walking, and is mounted between a user's thigh and a prosthetic shank. When the user walks, the user stamps on the ground mainly by his heels, such that the user can walk with the assistance of the conventional prosthetic knee joints. To prevent the user from experiencing discomfort or falling when walking (upstairs or downstairs and on a rough road), the conventional prosthetic knee joint provides effects of buffering and avoiding over-bending that makes the user fall.

However, to provide said effects of buffering and over-bending avoidance, the conventional prosthetic knee joint mainly comprises an upper connecting base, a lower connecting base, a linking assembly and a hydraulic cylinder assembly. The upper connecting base is connected to the user's thigh and has a side connecting point and a lower connecting point. The lower connecting base and the upper connecting base are connected to each other and are connected to a prosthetic shank. The lower connecting base has two upper linking points and a lower linking point. One of the two upper linking points of the lower connecting base is pivotally connected to the lower connecting point of the upper connecting base. The linking assembly is mounted between the upper connecting base and the lower connecting base. A top of the linking assembly is pivotally connected to the side connecting point of the upper connecting base. A bottom of the linking assembly is connected to the other upper linking point of the lower connecting base. The hydraulic cylinder assembly is mounted in the lower connecting base. A bottom of the hydraulic cylinder assembly is connected to the lower linking point of the lower connecting base. A top of the hydraulic cylinder assembly is connected to the bottom of the linking assembly, and is offset with the upper linking point of the lower connecting base.

The above connecting structure of the conventional prosthetics knee joint forms a five-bar linkage, such that the conventional prosthetic knee joint can change the position of the axis to provide the effects of buffering and over-bending avoidance when the user walks. However, the five-bar linkage comprises so many components, increasing the whole weight and complexity in connection. Therefore, it is inconvenient in assembly and in maintenance, which may raise the cost. As a result, the conventional prosthetic knee joint should be improved.

To overcome the shortcomings, the present invention provides a prosthetic knee joint with buffering and braking effects to mitigate or obviate the aforementioned problems.

SUMMARY OF THE INVENTION

The main objective of the present invention is to provide a prosthetic knee joint with buffering and braking effects that has simplified structure with a four-bar linkage and can provide a buffering effect to prevent the user from falling during walking.

The prosthetic knee joint with buffering and braking effects has
  an upper connecting base having
    two extending arms respectively formed on two sides of the upper connecting base and extending backward out of the upper connecting base; and
    an accommodating recess longitudinally formed through the upper connecting base and disposed between the two extending arms;
  a linking assembly pivotally connected to the upper connecting base and having
    two linking arms respectively disposed on outer sides of the extending arms, and top ends of the two linking arms respectively and pivotally connected to the upper connecting base;
  a braking assembly pivotally connected to the two extending arms of the upper connecting base, disposed next to the linking assembly, and having
    a braking arm, a top end of the braking arm protruding into the accommodating recess of the upper connecting base and pivotally connected to the two extending arms; and
  a lower connecting base connected to the linking assembly and the braking assembly, and having
    a main body connected to the two linking arms, and having
      two connecting protruding arms formed on a top end of the main body and disposed apart from each other;
      a receiving recess formed between the two connecting protruding arms; and
      a groove disposed in back of the two connecting protruding arms;
    an abutting element connected to the main body, being capable of swinging relative to the main body, disposed between the two connecting protruding arms, connected to the two linking arms, and having
      a front end disposed in the receiving recess;
      a swinging recess formed in a top end of the abutting element, a bottom end of the braking arm disposed in the swinging recess and connected to the abutting element; and
      a rear end protruding to be disposed above the groove; and
    a cushion mounted in the groove and abutting a bottom of the abutting element.

With the above technical features, the prosthetic knee joint with buffering and braking effects of the present invention mainly forms a four-bar linkage from the upper connecting base, the linking assembly, the braking assembly and the lower connecting base. The cushion between the abutting element and the main body provides a buffering effect during walking, and the components abut and are pivotally connected to each other to be limited in position to prevent the prosthetic knee joint from over-bending and making the user fall. As a result, the prosthetic knee joint may have reduced components and weight, and the connections between the components are simplified, thereby facilitating convenience in assembly and maintenance to reduce the cost. Thus, the present invention provides a prosthetic knee joint that has simplified structure and reduced cost and is convenient in assembly and use.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
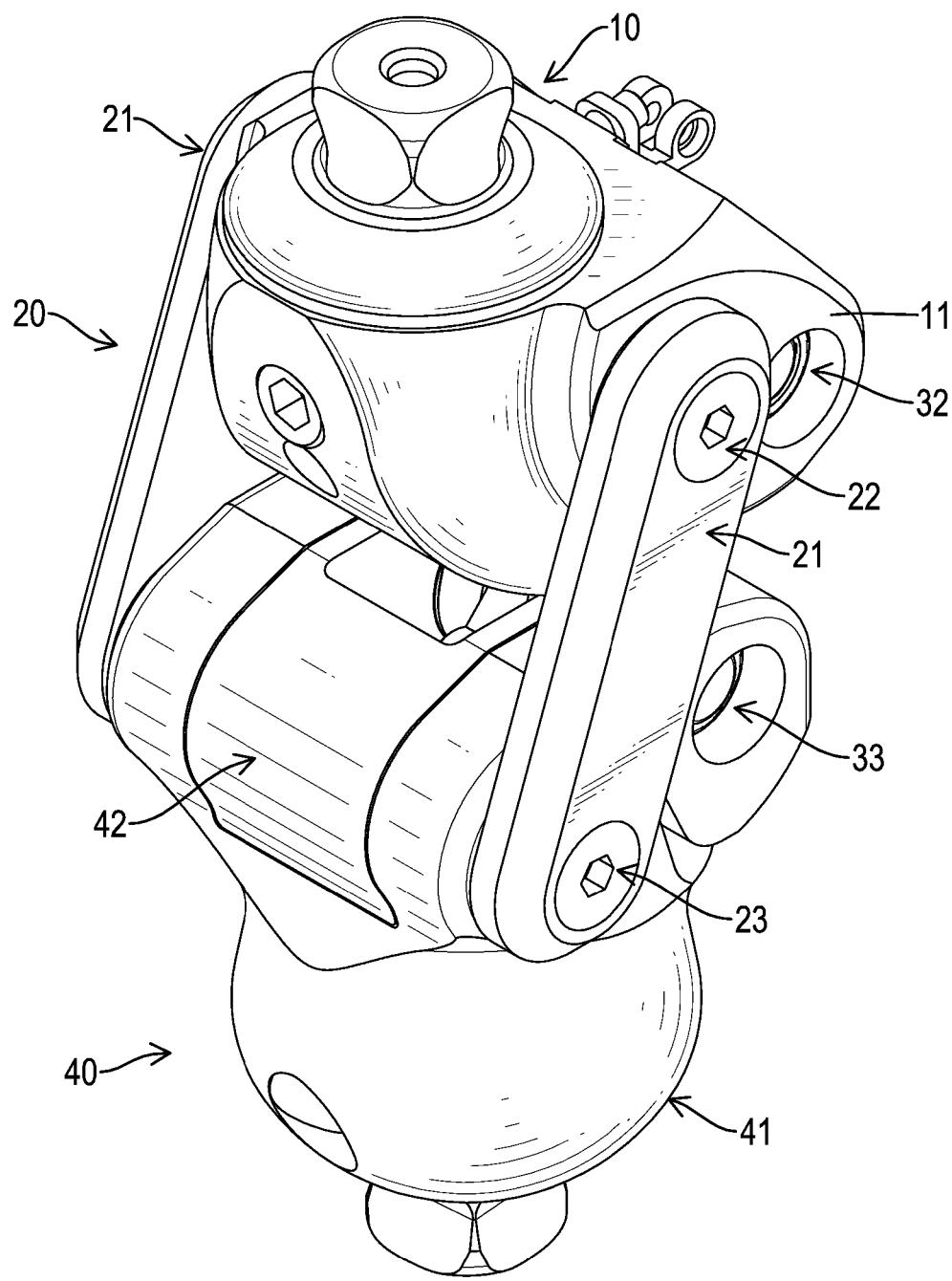
FIG. 1 is a perspective view of a prosthetic knee joint with buffering and braking effects in accordance with the present invention.
Figure 2:
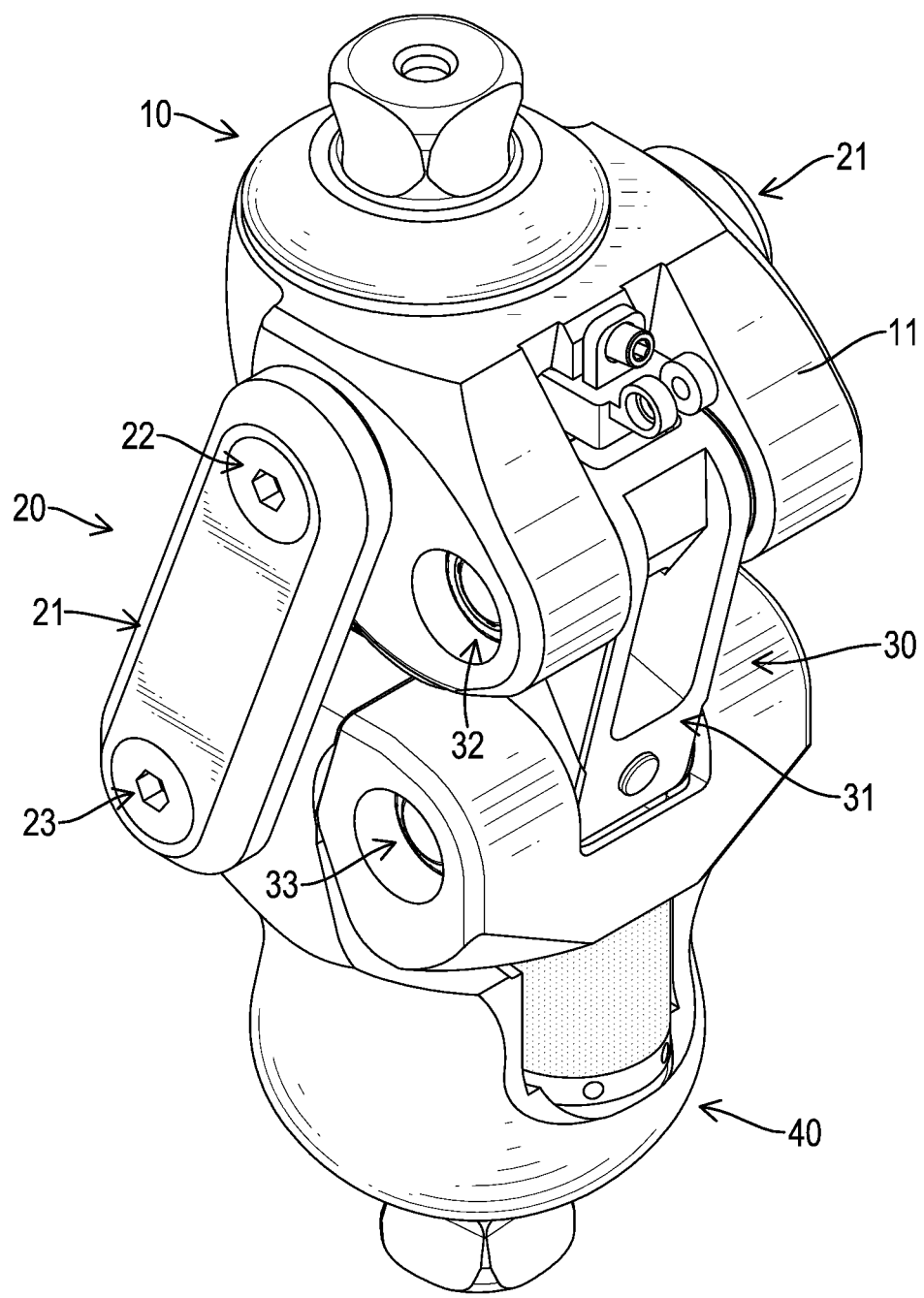
FIG. 2 is another perspective view of the prosthetic knee joint with buffering and braking effects in FIG. 1.

With reference to FIGS. 1 and 2, a prosthetic knee joint with buffering and braking effects in accordance with the present invention comprises an upper connecting base 10, a linking assembly 20, a braking assembly 30 and a lower connecting base 40.

Figure 3:
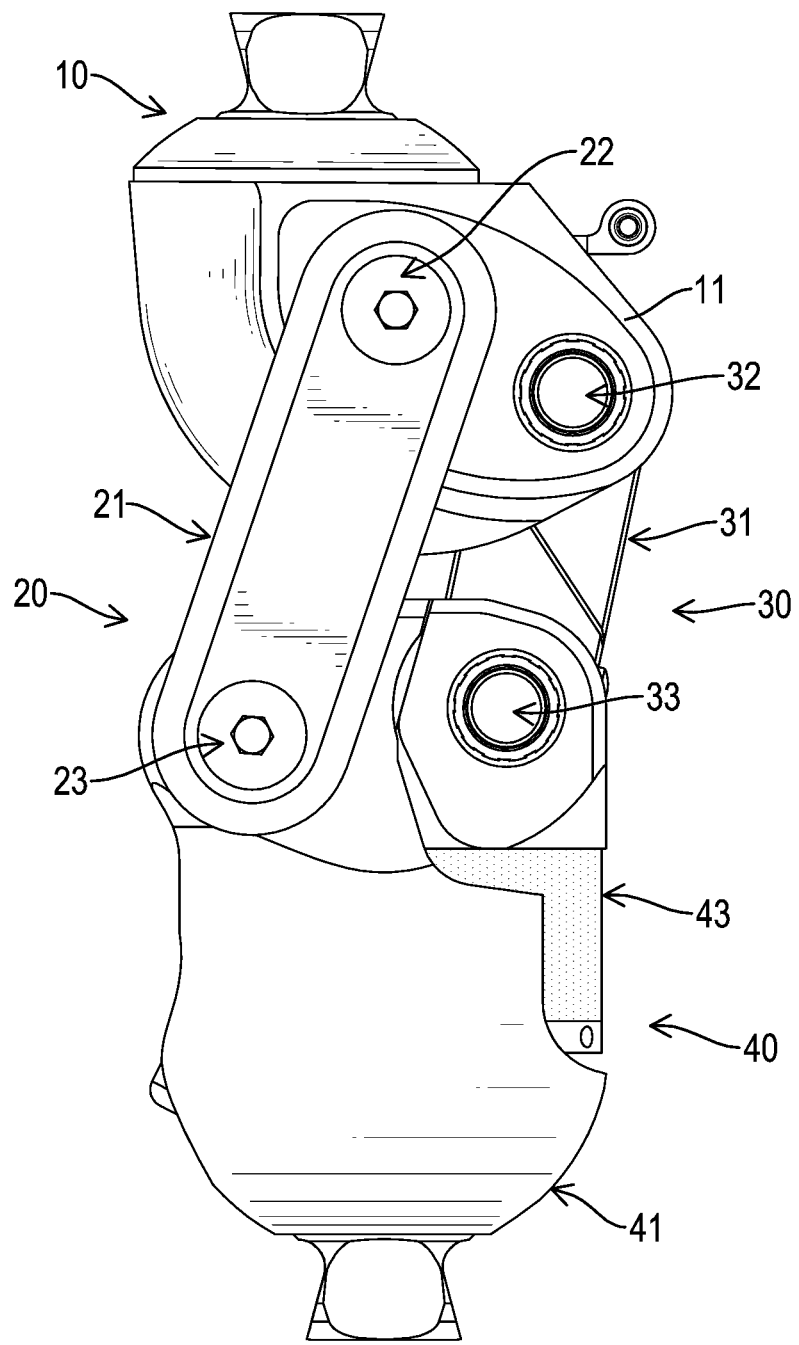
FIG. 3 is a side view of the prosthetic knee joint with buffering and braking effects in FIG. 1.
Figure 4:
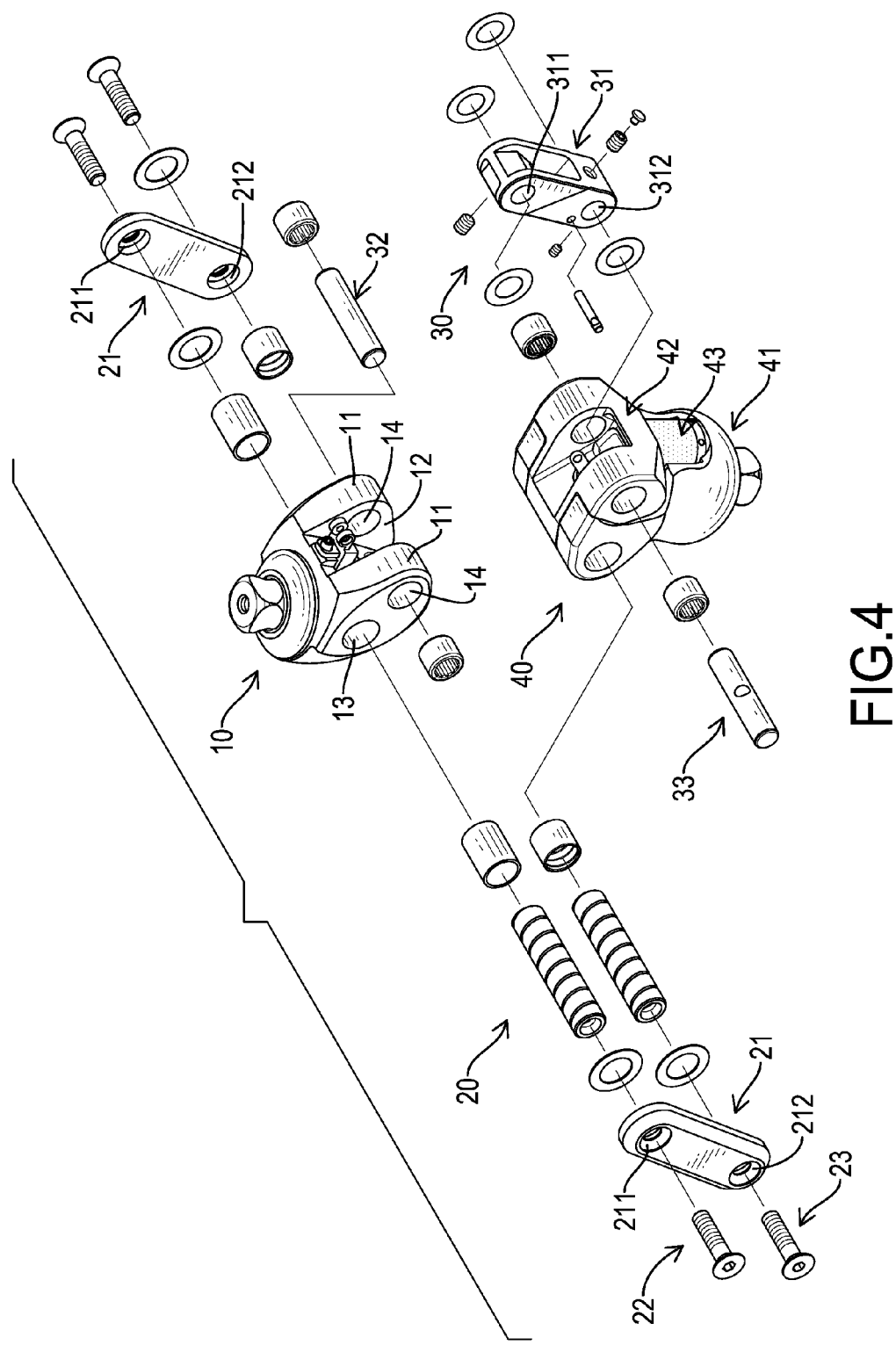
FIG. 4 is an exploded perspective view of the prosthetic knee joint with buffering and braking effects in FIG. 1.

With reference to FIGS. 3 and 4, the upper connecting base 10 is for connecting to a user's thigh, and has two extending arms 11, an accommodating recess 12, a first pivot hole 13 and two second pivot holes 14. The two extending arms 11 are respectively formed on two sides of the upper connecting base 10, extend backward out of the upper connecting base 10, and are parallel to each other. The accommodating recess 12 is longitudinally formed through the upper connecting base 10 and is disposed between the two extending arms 11. The first pivot hole 13 is transversely formed through the upper connecting base 10. The two second pivot holes 14 are respectively formed through two rear ends of the two extending arms 11 and communicate with the accommodating recess 12.

The linking assembly 20 is pivotally connected to the upper connecting base 10 and has two linking arms 21, a first pivot element 22, and a second pivot element 23. The two linking arms 21 are respectively disposed on outer sides of the extending arms 11. Each of the linking arms 21 has an upper pivot hole 211 and a lower pivot hole 212. The two upper pivot holes 211 of the two linking arms 21 are aligned with the first pivot hole 13 of the upper connecting base 10. The first pivot element 22 is mounted between the upper pivot holes 211 of the two linking arms 21 and the first pivot hole 13 of the upper connecting base 10 to pivotally connect the two linking arms 21 and the upper connecting base 10. The second pivot element 23 is mounted through the two lower pivot holes 212 of the two linking arms 21. The first pivot element 22 and the second pivot element 23 may respectively comprise multiple screws, gaskets and sleeves, which are conventional techniques for a person having ordinary skill in the art, and thus are not described in detail.

Figure 6:
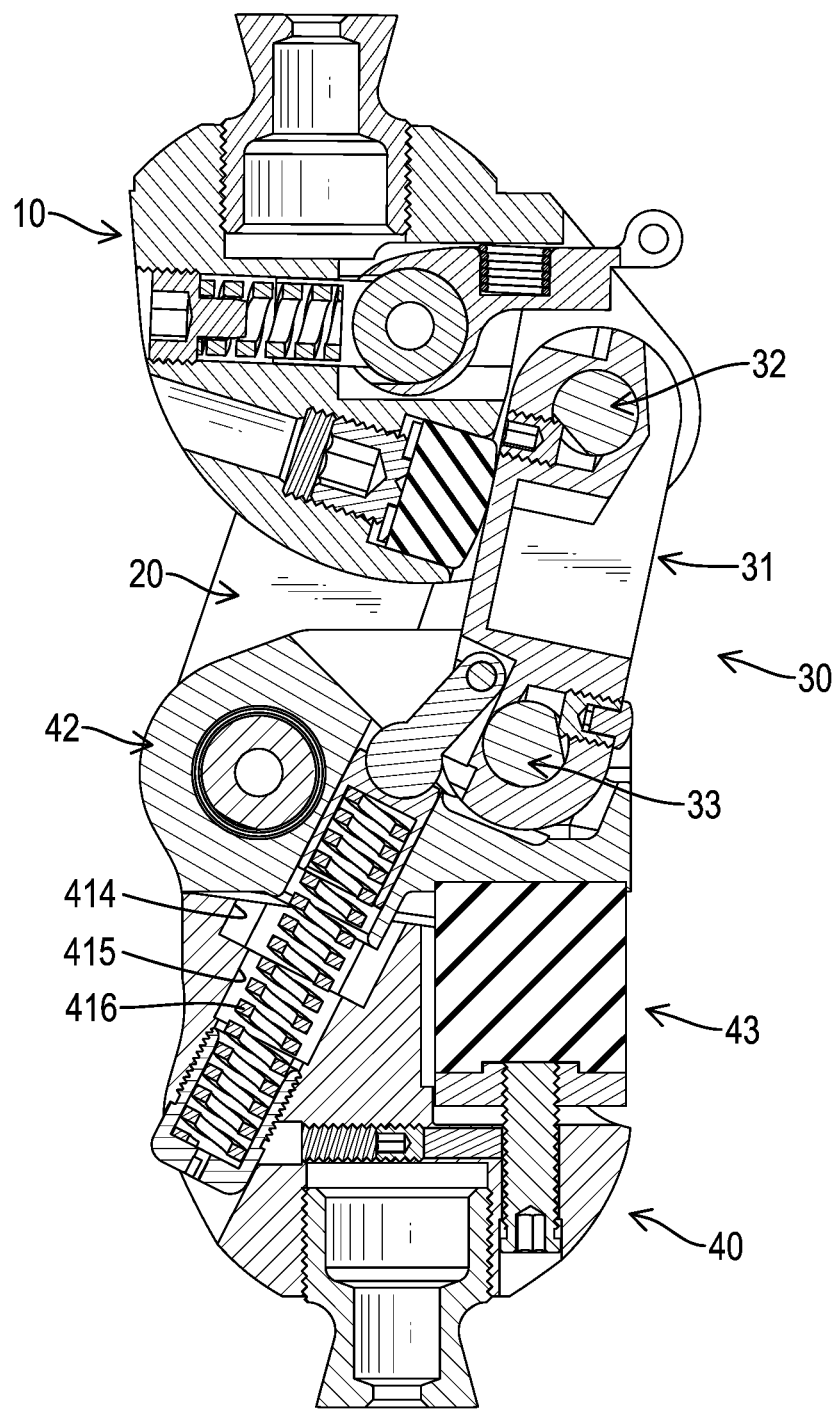
FIG. 6 is a side view in partial section of the prosthetic knee joint with buffering and braking effects in FIG. 1.

The braking assembly 30 is pivotally connected to the upper connecting base 10, is disposed next to the linking assembly 20, and has a braking arm 31, an upper pivot rod 32 and a lower pivot rod 33. A top end of the braking arm 31 protrudes into the accommodating recess 12 of the upper connecting base 10 and is disposed between the two extending arms 11. The braking arm 31 has an upper mounting hole 311 and a lower mounting hole 312. The upper mounting hole 311 is transversely formed through the top end of the braking arm 31 and is aligned with the two second pivot holes 14. The lower mounting hole 312 is transversely formed through the bottom end of the braking arm 31. The upper pivot rod 32 is mounted through the two second pivot holes 14 and the upper mounting hole 311 to pivotally connect the braking arm 31 and the upper connecting base 10. The lower pivot rod 33 is mounted through the lower mounting hole 312 of the braking arm 31. With reference to FIG. 6, the upper connecting base 10 has a pad mounted on an inner wall of the upper connecting base 10 and attached to the braking arm 31.

Figure 5:
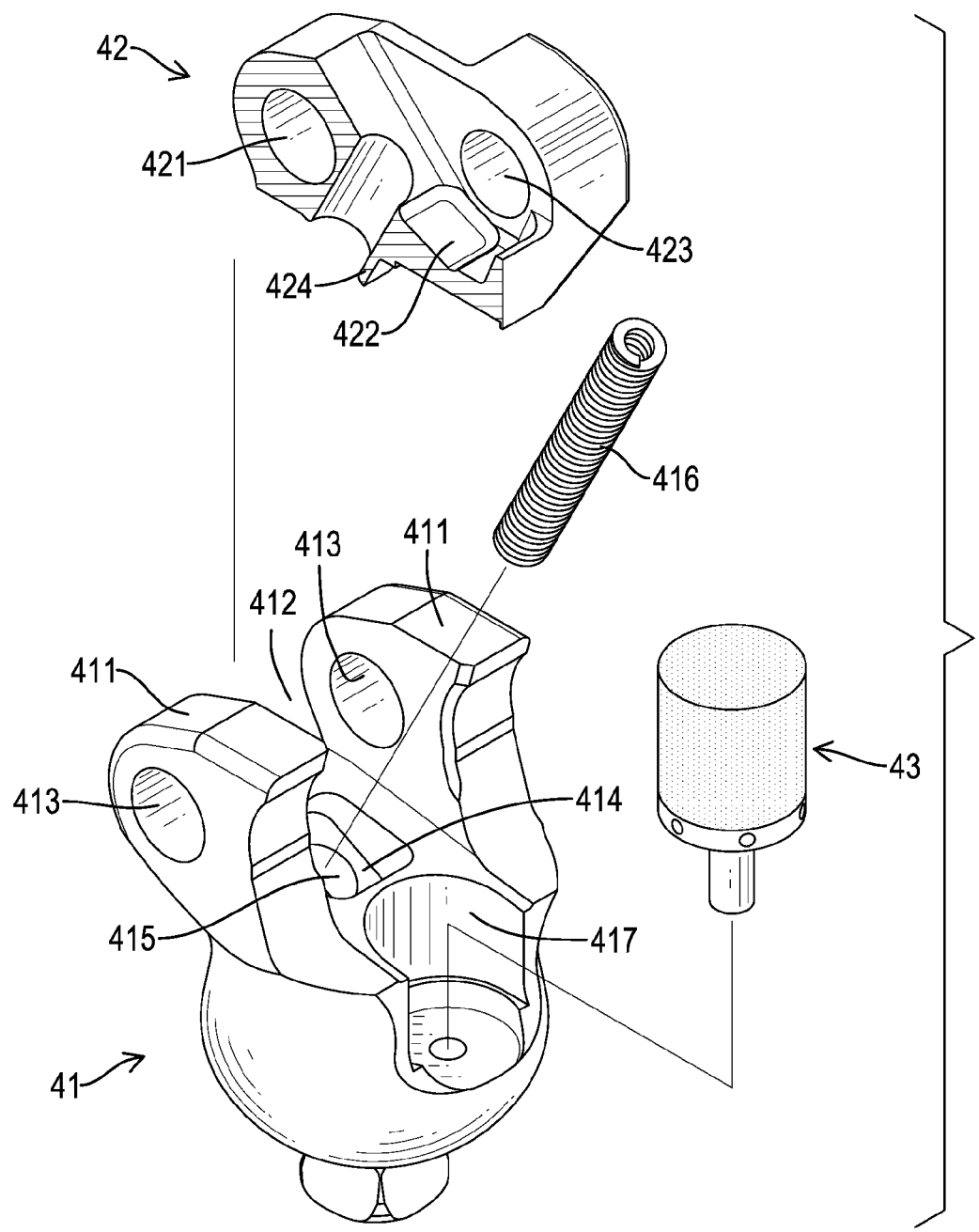
FIG. 5 is another exploded perspective view of the prosthetic knee joint with buffering and braking effects in FIG. 1.

With reference to FIGS. 4, 5 and 6, the lower connecting base 40 is connected to the linking assembly 20 and the braking assembly 30, and has a main body 41, an abutting element 42, and a cushion 43. The main body 41 has two connecting protruding arms 411, a receiving recess 412, an aligning hole 414, a mounting recess 415, a resilient element 416, and a groove 417. The two connecting protruding arms 411 are formed on a top end of the main body 41, and are disposed apart from each other. The receiving recess 412 is formed between the two connecting protruding arms 411. Each of the connecting protruding arms 411 has a body through hole 413 transversely formed through the connecting protruding arm 411 and communicating with the receiving recess 412. The two body through holes 413 of the two connecting protruding arms 411 are aligned with each other. The aligning hole 414 is substantially rectangular and is formed in a bottom of the receiving recess 412. The mounting recess 415 is disposed inside the main body 41 and communicates with the aligning hole 414. The resilient element 416 is mounted in the mounting recess 415 and the aligning hole 414 and disposed between the two connecting protruding arms 411. The groove 417 is disposed in back of the two connecting protruding arms 411.

The abutting element 42 is connected to the main body 41, is capable of swinging relative to the main body 41, and is disposed between the two connecting protruding arms 411. A front end of the abutting element 42 is disposed in the receiving recess 412 of the main body 41. The abutting element 42 has an abutting element through hole 421, a swinging recess 422, and a connecting hole 423. The abutting element through hole 421 is transversely formed through the front end of the abutting element 42 and is aligned with the two body through holes 413. The second pivot element 23 is mounted through the lower pivot holes 212 of the two linking arms 21, the body through holes 413 of the two connecting protruding arms 411, and the abutting element through hole 421 of the abutting element 42 to simultaneously connect the two linking arms 21 to the main body 41 and the abutting element 42. The swinging recess 422 is obliquely formed in a top end of the abutting element 42, such that the bottom end of the braking arm 31 is disposed in the swinging recess 422 to make the lower mounting hole 312 of the braking arm 31 mounted in the swinging recess 422. The connecting hole 423 is transversely formed through the abutting element 42, is disposed adjacent to a rear end of the abutting element 42, communicates with the swinging recess 422, and is aligned with the lower mounting hole 312 of the braking arm 31. The lower pivot rod 33 is mounted through the connecting hole 423, the swinging recess 422, and the lower mounting hole 312 to connect the braking arm 31 and the abutting element 42. The rear end of the abutting element 42 protrudes to be disposed above the groove 417. The abutting element 42 has a sleeve 424. The sleeve 424 protrudes obliquely from the bottom of the abutting element 42, is disposed adjacent to the front end of the abutting element 42, and is mounted in the aligning hole 414 of the main body 41 to make the resilient element 416 connected to the braking arm 31 via the aligning hole 414 and the sleeve 424 of the abutting element 42. The cushion 43 is mounted in the groove 417 and abuts the bottom of the abutting element 42.

Figure 7:
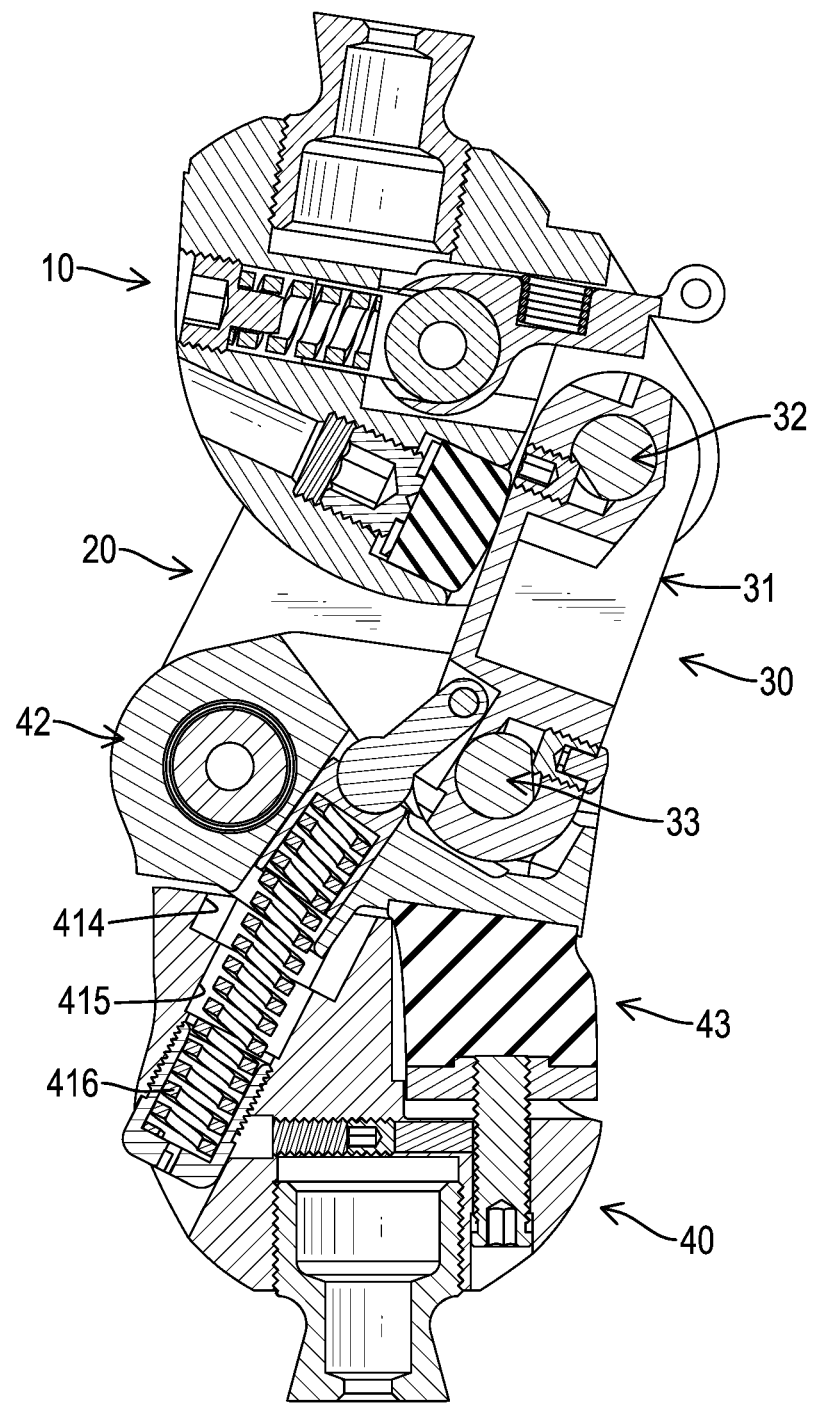
FIG. 7 is a side view in partial section of the prosthetic knee joint with buffering and braking effects in FIG. 1, shown in use.

The prosthetic knee joint with buffering and braking effects of the present invention in use is as shown in FIG. 7. The user's thigh and a prosthetic shank (not shown in the figures) are respectively connected to the upper connecting base 10 and the lower connecting base 40. When the user walks and stamps on the ground by his heels, the weight of the user and the counterforce from the ground abut the braking arm 31 via the pad inside of the upper connecting base 10 to swing the lower connecting base 40. The force then transmits to the cushion 43 via the abutting element 42 and the main body 41 to make the braking arm 31 push and rotate the abutting element 42 relative to the main body 41 to press the cushion 43, thereby providing a buffering effect during walking. The upper connecting base 10, the linking assembly 20, the braking assembly 30 and the lower connecting base 40 form a four-bar linkage, and the components abut and are pivotally connected to each other to be limited in position, thereby preventing the prosthetic knee joint from over-bending to make the user fall during walking, and providing a braking effect.

With the above technical features, the prosthetic knee joint with buffering and braking effects of the present invention mainly forms a four-bar linkage from the upper connecting base 10, the linking assembly 20, the braking assembly 30 and the lower connecting base 40. The cushion 43 between the abutting element 42 and the main body 41 provides a buffering effect during walking, and the components abut and are pivotally connected to each other to be limited in position to prevent the prosthetic knee joint from over-bending and making the user fall. As a result, the prosthetic knee joint can be reduced in components and weight, and the connections between the components are simplified, thereby facilitating convenience in assembly and maintenance to reduce the cost. Thus, the present invention provides a prosthetic knee joint that has simplified structure and reduced cost and is convenient in assembly and use.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:
1. A prosthetic knee joint with buffering and braking effects comprising:
   an upper connecting base having
      two extending arms respectively formed on two sides of the upper connecting base and extending backward out of the upper connecting base; and
      an accommodating recess longitudinally formed through the upper connecting base and disposed between the two extending arms;
   a linking assembly pivotally connected to the upper connecting base and having
      two linking arms respectively disposed on outer sides of the extending arms, and top ends of the two linking arms respectively and pivotally connected to the upper connecting base;
   a braking assembly pivotally connected to the two extending arms of the upper connecting base, disposed next to the linking assembly, and having
      a braking arm, a top end of the braking arm protruding into the accommodating recess of the upper connecting base and pivotally connected to the two extending arms; and
   a lower connecting base connected to the linking assembly and the braking assembly, and having
      a main body pivotally connected to the two linking arms, and having
         two connecting protruding arms formed on a top end of the main body and disposed apart from each other;
         a receiving recess formed between the two connecting protruding arms; and
         a groove disposed in back of the two connecting protruding arms;
      an abutting element connected to the main body, being capable of swinging relative to the main body, disposed between the two connecting protruding arms, pivotally connected to the two linking arms, and having
         a front end disposed in the receiving recess;
         a swinging recess formed in a top end of the abutting element, a bottom end of the braking arm disposed in the swinging recess and pivotally connected to the abutting element; and
         a rear end protruding to be disposed above the groove; and
      a cushion mounted in the groove and abutting a bottom of the abutting element at a position corresponding to and below a pivot junction between the abutting element and the braking arm.

2. The prosthetic knee joint with buffering and braking effects as claimed in claim 1, wherein
   the upper connecting base has
      a first pivot hole transversely formed through the upper connecting base;
   each of the linking arms has
      an upper pivot hole aligned with the first pivot hole of the upper connecting base; and
   the linking assembly has
      a first pivot element mounted between the upper pivot holes of the two linking arms and the first pivot hole of the upper connecting base to pivotally connect the two linking arms and the upper connecting base.

3. The prosthetic knee joint with buffering and braking effects as claimed in claim 2, wherein
   the upper connecting base has
      two second pivot holes respectively formed through two rear ends of the two extending arms and communicating with the accommodating recess;
   each of the linking arms has
      a lower pivot hole; and
   the linking assembly has
      a second pivot element mounted through the two lower pivot holes of the two linking arms.

4. The prosthetic knee joint with buffering and braking effects as claimed in claim 3, wherein
the braking arm has
an upper mounting hole transversely formed through the top end of the braking arm and aligned with the two second pivot holes; and
the braking assembly has
an upper pivot rod mounted through the two second pivot holes and the upper mounting hole to pivotally connect the braking arm and the upper connecting base.

5. The prosthetic knee joint with buffering and braking effects as claimed in claim 4, wherein
the braking arm has
a lower mounting hole transversely formed through the bottom end of the braking arm; and
the braking assembly has
a lower pivot rod mounted through the lower mounting hole.

6. The prosthetic knee joint with buffering and braking effects as claimed in claim 5, wherein
each of the connecting protruding arms has
a body through hole transversely formed through the connecting protruding arm and communicating with the receiving recess;
the abutting element has
an abutting element through hole transversely formed through the front end of the abutting element and aligned with the two body through holes of the two connecting protruding arms; and
the second pivot element is mounted through the two lower pivot holes of the two linking arms, the two body through holes of the two connecting protruding arms, and the abutting element through hole of the abutting element.

7. The prosthetic knee joint with buffering and braking effects as claimed in claim 6, wherein
the lower mounting hole of the braking arm is disposed in the swinging recess;
the abutting element has
a connecting hole transversely formed through the abutting element, disposed adjacent to the rear end of the abutting element, communicating with the swinging recess, and aligned with the lower mounting hole of the braking arm; and
the lower pivot rod is mounted through the connecting hole, the swinging recess, and the lower mounting hole to connect the braking arm and the abutting element.

8. The prosthetic knee joint with buffering and braking effects as claimed in claim 7, wherein
the main body has
an aligning hole formed in a bottom of the receiving recess; and
the abutting element has
a sleeve protruding obliquely from the bottom of the abutting element, disposed adjacent to the front end of the abutting element, and mounted in the aligning hole of the main body.

9. The prosthetic knee joint with buffering and braking effects as claimed in claim 8, wherein
the main body has
a mounting recess disposed inside the main body and communicating with the aligning hole; and
a resilient element mounted in the mounting recess, the aligning hole, and the sleeve to be connected to the braking arm.

\* \* \* \* \*